US012661527B2

(12) United States Patent
Wiberg et al.

(10) Patent No.: US 12,661,527 B2
(45) Date of Patent: Jun. 23, 2026

(54) DEVICES AND METHODS FOR DELIVERING NON-COPLANAR RADIOTHERAPY

(71) Applicant: Elekta Limited, Crawley (GB)

(72) Inventors: Kristian Wiberg, Crawley (GB); Per Carlsson, Crawley (GB)

(73) Assignee: Elekta Limited, Crawley (GB)

( * ) Notice: Subject to any disclaimer, the term of this patent is extended or adjusted under 35 U.S.C. 154(b) by 255 days.

(21) Appl. No.: 18/259,180

(22) PCT Filed: Dec. 16, 2021

(86) PCT No.: PCT/GB2021/053336
§ 371 (c)(1),
(2) Date: Jun. 23, 2023

(87) PCT Pub. No.: WO2022/136839
PCT Pub. Date: Jun. 30, 2022

(65) Prior Publication Data
US 2024/0050771 A1 Feb. 15, 2024

(30) Foreign Application Priority Data

Dec. 24, 2020 (GB) ...................................... 2020625

(51) Int. Cl.
*A61N 5/10* (2006.01)
(52) U.S. Cl.
CPC ......... *A61N 5/1047* (2013.01); *A61N 5/1065* (2013.01); *A61N 5/1081* (2013.01)
(58) Field of Classification Search
None
See application file for complete search history.

(56) References Cited

U.S. PATENT DOCUMENTS 4,419,585 A * 12/1983 Strauss .................. G21K 1/025
976/DIG. 429
4,726,046 A 2/1988 Nunan
(Continued)

FOREIGN PATENT DOCUMENTS

CN 210433857 U 5/2020
EP 2995347 A1 3/2016
WO WO-2018090196 A1 5/2018

OTHER PUBLICATIONS

"International Application Serial No. PCT/GB2021/053336, International Search Report dated Mar. 30, 2022", (Mar. 30, 2022), 4 pgs.
(Continued)

*Primary Examiner* — Marcus H Taningco
(74) *Attorney, Agent, or Firm* — Schwegman Lundberg & Woessner, P.A.

(57) ABSTRACT

A radiotherapy apparatus is described. The radiotherapy apparatus comprises a radiation source, a beam shaping apparatus, a beam receiving apparatus, and a controller configured to control the beam shaping apparatus. The radiation source is configured to deliver radiation in each of a coplanar configuration and at least one non-coplanar configuration. The beam shaping apparatus is configured to direct the radiation produced by the radiation source towards the beam receiving apparatus in each of the coplanar configuration and the at least one non-coplanar configuration. The controller is configured to control the beam shaping apparatus to apply a limit on a field of radiation produced by the radiation source based on whether the radiation source is configured in the coplanar configuration or the at least one non-coplanar configuration.

19 Claims, 7 Drawing Sheets

(56) References Cited

U.S. PATENT DOCUMENTS

| | | | |
|---|---|---|---|
| 2004/0005027 A1 | 1/2004 | Näfstadius | |
| 2007/0195936 A1 | 8/2007 | Manthey et al. | |
| 2007/0211856 A1* | 9/2007 | Urano | A61N 5/1049 |
| | | | 378/65 |
| 2007/0297566 A1* | 12/2007 | Urano | A61N 5/1049 |
| | | | 378/65 |
| 2008/0170663 A1* | 7/2008 | Urano | A61N 5/1049 |
| | | | 378/65 |
| 2012/0189102 A1 | 7/2012 | Maurer, Jr. et al. | |
| 2013/0158382 A1 | 6/2013 | Chao | |
| 2013/0261430 A1* | 10/2013 | Uhlemann | A61N 5/1077 |
| | | | 378/65 |
| 2016/0074673 A1* | 3/2016 | Allen | A61N 5/1049 |
| | | | 600/1 |
| 2017/0246477 A1* | 8/2017 | Zhang | A61N 5/1047 |
| 2020/0164225 A1* | 5/2020 | Zhang | A61N 5/1031 |
| 2022/0163466 A1* | 5/2022 | Gateshki | G21K 1/046 |
| 2023/0015121 A1* | 1/2023 | Sheng | A61B 5/0037 |
| 2023/0241419 A1* | 8/2023 | Maltz | A61N 5/1049 |
| | | | 378/19 |

OTHER PUBLICATIONS

"United Kingdom Application Serial No. 2020625.6, Examination Report dated May 26, 2021", (May 26, 2021), 4 pgs.

"European Application No. 21 839 611.7, Examination Report dated Jul. 8, 2025", (Jul. 8, 2025), 6 pgs.

* cited by examiner

DEVICES AND METHODS FOR DELIVERING NON-COPLANAR RADIOTHERAPY

PRIORITY APPLICATIONS

This application is a U.S. National Stage Filing under 35 U.S.C. § 371 from International Application No. PCT/GB2021/053336, filed on Dec. 16, 2021, and published as WO2022/136839 on Jun. 30, 2022, which claims the benefit of priority to British Application No. 2020625.6, filed on Dec. 24, 2020; the benefit of priority of each of which is hereby claimed herein, and which applications and publication are hereby incorporated herein by reference in their entireties.

FIELD

The present disclosure relates to a radiotherapy apparatus configured to deliver radiation to a subject, and associated methods. More specifically, the present disclosure relates to a radiotherapy apparatus configured to deliver radiation at a tilted angle relative to the subject.

BACKGROUND

When delivering a beam of radiation a patient, it is desirable to deliver the radiation from multiple angles, to minimise the effect of the radiation on healthy tissue. One way of achieving this known in the art is by rotating the radiation source about the patient, for example about a longitudinal axis of the patient, such that radiation can be delivered to the patient from many angles in a plane perpendicular to the longitudinal axis. Treatments that employ rotation of the radiation source solely in this manner are known as coplanar. A further degree of freedom is achieved by tilting the radiation source outside of the plane perpendicular to the patient's longitudinal axis, such that radiation is delivered at an oblique angle relative to the longitudinal axis. This helps increase the number of angles at which radiation can be delivered to the patient, thereby minimising the effect on healthy tissue.

As is known in the art, a beam stopper (also known as a beam shield) and/or detector is typically positioned opposite the source of radiation, i.e. on the opposite side of the patient to the radiation source during treatment, to attenuate/detect a beam of radiation after the beam has passed through the patient. The beam stopper and/or detector may be mounted on a rotating ring gantry along with the radiation source, with the beam stopper and/or detector placed diametrically opposite the radiation source. However, in the case of tilting the radiation source outside of the gantry plane, the beam stopper/detector also needs to be tilted accordingly to ensure the beam stopper/detector is positioned in the path of the beam of radiation. This requires additional mechanisms capable of tilting the beam stopper/detector, or else the entire ring gantry must be tilted. Thus, prior devices capable of delivering both coplanar and non-coplanar treatment are typically extremely large and heavy. Both the cost and complexity of these known prior systems is high. Complex counterweight systems may be required. Prior designs are not only large but take up a large amount of space by virtue of the tiltable gantry or the tiltable beam stopper and/or detector.

Implementations of the present disclosure seeks to address these and other problems encountered in the prior art.

SUMMARY

Aspects and features of the present invention are described in the accompanying claims.

One aspect of the present invention provides a radiotherapy apparatus, comprising a radiation source, a beam shaping apparatus, a beam receiving apparatus and a controller to control the beam shaping apparatus. The radiation source is configured to deliver radiation in each of a coplanar configuration and at least one non-coplanar configuration, the beam shaping apparatus is configured to direct the radiation produced by the radiation source towards the beam receiving apparatus in each of the coplanar configuration and the at least one non-coplanar configuration; and the controller is configured to control the beam shaping apparatus to apply a limit on a field of radiation produced by the radiation source based on whether the radiation source is configured in the coplanar configuration or the at least one non-coplanar configuration.

The beam receiving apparatus may comprise at least one of a beam stopper and a radiation detector.

The controller may be configured to determine a spread of the radiation field using signals from the radiation detector, and control the beam shaping apparatus to reduce the spread of the field if the determined spread of the radiation field is within a threshold distance from the edge of the radiation detector.

In some embodiments, the controller can be configured to control the beam shaping apparatus such that all of the radiation in the field of radiation is incident on the beam receiving apparatus.

The controller can be configured to follow an operational rule defining a limit of retraction of at least one beam shaping member of the beam shaping apparatus when in the non-coplanar configuration.

The application of the operational rule may be dependent on whether the radiation source is in the coplanar or non-coplanar configuration.

The beam shaping member can be one of a diaphragm and a leaf of an MLC. The beam shaping apparatus may be an MLC and the limit may be applied such that, in the non-coplanar configuration, one leaf, or a plurality of adjacent leaves, of the MLC may have a limit of retraction such that the leaf or leaves may not retract from a maximum extension into the radiation field.

In some embodiments, the controller may be further configured to control the radiation source.

The controller may be configured to switch the radiotherapy apparatus between a first and second mode. In the first mode, the radiation source is in the coplanar configuration and in the second mode, the radiation source is in a non-coplanar configuration.

The controller may be configured to control the beam shaping apparatus to adjust an angle of the field of radiation relative to the rotation axis.

The radiation source may be positioned to rotate about a rotation axis and in a first plane when in the coplanar configuration.

In the non-coplanar configuration, the radiation source may be non-coplanar with respect to the first plane such that the field of radiation produced by the radiation source is directed at an oblique angle relative to the first plane and the rotation axis.

In at least one non-coplanar configuration, the radiation source may be positioned to rotate in a respective second plane parallel to and displaced from the first plane.

The radiotherapy apparatus may further comprise a rotatable gantry configured to rotate about the rotation axis, and wherein the radiation source and beam receiving apparatus are mounted on opposite sides of the gantry.

In the at least one non-coplanar configurations, the radiation source may be configured to direct the field of radiation at an oblique angle relative to the rotation axis.

The controller may be configured to control the beam shaping apparatus to adjust or modify the angle of the field of radiation relative to the rotation axis when the radiation source is in the non-coplanar configuration.

The controller may be configured to control the beam shaping apparatus to increase the angle of the field of radiation relative to the rotation axis when the radiation source is in the non-coplanar configuration.

The controller can be configured to control the beam shaping apparatus to apply the limit when the radiation source is in the at least one non-coplanar configuration and to remove the limit when the radiation source is in the coplanar configuration.

Another aspect of the present invention concerns a method of controlling a field of radiation produced by a radiation source of a radiotherapy apparatus, the method comprising switching the radiation source between a coplanar configuration and a non-coplanar configuration, and applying a limit to the field of radiation produced by the radiation source based on whether the radiation source is configured in the coplanar configuration or the non-coplanar configuration. The limit is applied to the field of radiation such that the radiation produced by the radiation source is directed towards a beam receiving apparatus in each of the coplanar and at least one non-coplanar configuration.

The limit can be applied to the field of radiation such that the radiation produced by the radiation source is directed towards a beam receiving apparatus in each of the coplanar configuration and at least one non-coplanar configurations.

The field of radiation may be limited such that all of the radiation in the field of radiation is incident on the beam receiving apparatus.

The field of radiation may be controlled by applying an operational rule defining a limit of retraction of at least one beam shaping member of the beam shaping apparatus.

The application of the operational rule may be dependent on whether the radiation source is in the coplanar configuration or the non-coplanar configuration.

The method may further comprise applying the limit when the radiation source is in the at least one non-coplanar configuration and removing the limit when the radiation source is in the coplanar configuration.

In some embodiments, the beam shaping apparatus may be an MLC and the limit is applied such that, in the non-coplanar configuration, one leaf, or a plurality of adjacent leaves, of the MLC may have a limit of retraction such that the leaf or leaves may not retract from a maximum extension into the radiation field.

In another aspect of the present disclosure, a computer-readable medium is provided which comprises instructions that, when executed by one or more processors, cause the processors to carry out any of the methods disclosed herein.

BRIEF DESCRIPTION OF THE DRAWINGS

Specific implementations are described below by way of example only and with reference to the accompanying drawings in which.

DETAILED DESCRIPTION

Overview—Radiotherapy Apparatus

Aspects of the disclosure will be described below. In overview, and without limitation, the present application relates to a radiotherapy apparatus which has both coplanar and non-coplanar (e.g. tilted) modes. The radiotherapy apparatus includes a radiation source and a beam shaping apparatus such as an MLC, which is connected to a controller. The controller is configured to control the beam shaping apparatus to apply a limit on a field of radiation produced by the radiation source based on whether the radiation source is configured in the coplanar configuration or the at least one non-coplanar configuration. This may improve or increase the amount of radiation incident on a beam receiving means in both coplanar and non-coplanar modes, for example without having to move the longitudinal position of the beam receiving means or increase the size of the beam receiving means and apparatus. In some embodiments, the beam receiving means can be moved to a lesser degree than the movement of the radiation source.

Figure 1:
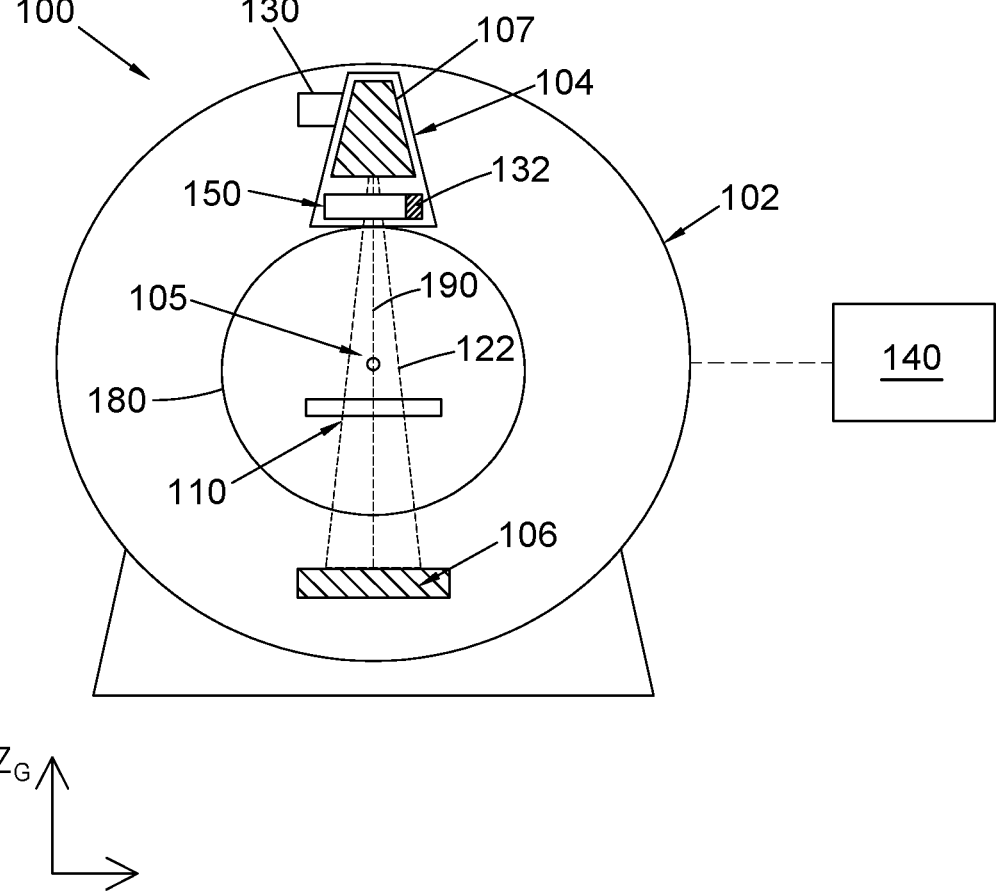
FIG. 1 depicts a radiotherapy apparatus.

FIG. 1 depicts a radiotherapy apparatus according to the present disclosure. The Figure shows a cross-section through a radiotherapy apparatus 100 comprising a radiation head 104 and a beam receiving apparatus 106, both of which are attached to a gantry 102. The radiation head 104 includes a radiation source 107 which emits a beam of radiation 122. The radiation head 104 also includes a beam shaping apparatus 150 which controls the size and shape of the radiation field associated with the beam.

The beam receiving apparatus 106 is configured to receive radiation emitted from the radiation head 104, for the purpose of absorbing and/or measuring the beam of radiation. In the view shown in FIG. 1, the radiation head 104 and the beam receiving apparatus 106 are positioned diametrically opposed to one another. However, in some embodiments, the radiation head 104 may be moved independently from the beam receiving apparatus 106. That is, in some embodiments, the radiation head 104 may be configured to move to a position which is not substantially diametrically opposed to the beam receiving apparatus 106.

The gantry 102 is rotatable, and supports the radiation head 104 and the beam receiving apparatus 106 such that they are rotatable around an axis of rotation 105, which may coincide with the patient longitudinal axis. As shown in FIG. 1, the gantry provides rotation of the radiation head 104 and the beam receiving apparatus 106 in a plane which is perpendicular to the patient longitudinal axis (e.g. a sagittal plane). Three gantry directions $X_G$, $Y_G$, $Z_G$ can be defined, where the $Y_G$ direction is perpendicular with gantry axis of rotation. The $Z_G$ direction extends from a point on the gantry corresponding to the radiation head, towards the axis of rotation of the gantry. Therefore, from the patient frame of reference, the $Z_G$ direction rotates around as the gantry rotates.

FIG. 1 also shows a support surface 110 on which a subject (or patient) is supported during radiotherapy treatment. The radiation head 104 is configured to rotate around the axis of rotation 105 such that the radiation head 104 directs radiation towards the subject from various angles around the subject in order to spread out the radiation dose received by healthy tissue to a larger region of healthy tissue while building up a prescribed dose of radiation at a target region.

The radiotherapy apparatus 100 is configured to deliver a radiation beam towards a radiation isocentre which is substantially located on the axis of rotation 105 at the centre of the gantry 102 regardless of the angle at which the radiation head 104 is placed.

The rotatable gantry 102 and radiation head 104 are dimensioned so as to allow a central bore 180 to exist. The central bore 180 provides an opening sufficient to allow a subject to be positioned therethrough without the possibility of being incidentally contacted by the radiation head 104 or other mechanical components as the gantry rotates the radiation head 104 about the subject.

As shown in FIG. 1, the radiation head 104 emits the radiation beam 122 along a beam axis 190 (or radiation axis or beam path), where the beam axis 190 is used to define the direction in which the radiation is emitted by the radiation head. The radiation beam 122 is incident on the beam receiving apparatus 106 which can include at least one of a beam stopper and a radiation detector. The beam receiving apparatus 106 is attached to the gantry 102 on a diametrically opposite side to the radiation head 104 in order to attenuate and/or detect a beam of radiation after the beam has passed through the subject. In some embodiments, the beam receiving apparatus 106 may be moved independently with respect to the radiation head 104—for example, the beam receiving apparatus 106 may be moved a lesser distance than the radiation head 104. That is, the beam receiving apparatus 106 may be configured to be moved to a position not diametrically opposed from the radiation head 104.

The radiation beam axis 190 may be defined as, for example, a centre of the radiation beam 122 or a point of maximum intensity.

The beam shaping apparatus 150 delimits the spread of the radiation beam 122. The beam shaping apparatus 150 is configured to adjust the shape and/or size of a field of radiation produced by the radiation source. The beam shaping apparatus 150 does this by defining an aperture (also referred to as a window) of variable shape to collimate the radiation beam 122 to a chosen cross-sectional shape. In this example, the beam shaping apparatus 150 is provided by a combination of a diaphragm and a multi-leaf collimator (MLC).

As explained further below, the radiotherapy apparatus 100 is configured to deliver both coplanar and non-coplanar (also referred to as tilted) modes of radiotherapy treatment. In coplanar treatment, radiation is emitted in a plane which is perpendicular to the axis of rotation of the radiation head 104. In non-coplanar treatment, radiation is emitted at an angle which is not perpendicular to the axis of rotation. In order to deliver coplanar and non-coplanar treatment, the radiation head 104 can move between at least two positions, one in which the radiation is emitted in a plane which is perpendicular to the axis of rotation (coplanar configuration) and at least one in which radiation is emitted in a plane which is not perpendicular to the axis of rotation (non-coplanar configuration).

In the coplanar configuration, the radiation head is positioned to rotate about a rotation axis and in a first plane. In the non-coplanar configuration, the radiation head is tilted with respect to the first plane such that a field of radiation produced by the radiation head is directed at an oblique angle relative to the first plane and the rotation axis. In the non-coplanar configuration, the radiation head is positioned to rotate in a respective second plane parallel to and displaced from the first plane. The radiation beam is emitted at an oblique angle with respect to the second plane, and therefore as the radiation head rotates the beam sweeps out a cone shape.

The beam receiving apparatus 106 may remain in the same place relative to the rotatable gantry when the radiotherapy apparatus is in both the coplanar and non-coplanar modes. Therefore, the beam receiving apparatus 106 may be configured to rotate about the rotation axis in the same plane in both coplanar and non-coplanar modes. This may be the same plane as the plane in which the radiation head rotates.

The beam shaping apparatus 150 is configured to reduce the spread of the field of radiation in the non-coplanar configuration in comparison to the coplanar configuration.

The radiotherapy apparatus 100 includes a controller 140 which is programmed to control the radiation source 107, beam receiving apparatus 106 and the gantry 102. Controller 140 may perform functions or operations such as treatment planning, treatment execution, image acquisition, image processing, motion tracking, motion management, and/or other tasks involved in a radiotherapy process.

Controller 140 is programmed to control features of apparatus 100 according to a radiotherapy treatment plan for irradiating a target tissue of a patient. The treatment plan includes information about a particular dose to be applied to a target tissue, as well as other parameters such as beam angles, dose-histogram-volume information, the number of radiation beams to be used during therapy, the dose per beam, and the like. Controller 140 is programmed to control various components of apparatus 100, such as gantry 102, radiation head 104, beam receiving apparatus 106, and support surface 110, according to the treatment plan.

Hardware components of controller 140 may include one or more computers (e.g., general purpose computers, workstations, servers, terminals, portable/mobile devices, etc.); processors (e.g., central processing units (CPUs), graphics processing units (GPUs), microprocessors, digital signal processors (DSPs), field programmable gate arrays (FPGAs), special-purpose or specially-designed processors, etc.); memory/storage devices such as a memory (e.g., read-only memories (ROMs), random access memories (RAMs), flash memories, hard drives, optical disks, solid-state drives (SSDs), etc.); input devices (e.g., keyboards, mice, touch screens, mics, buttons, knobs, trackballs, levers, handles, joysticks, etc.); output devices (e.g., displays, printers, speakers, vibration devices, etc.); circuitries; printed circuit boards (PCBs); or other suitable hardware. Software components of controller 140 may include operation device software, application software, etc.

The controller controls the beam shaping apparatus 150 based on whether the radiotherapy apparatus is in the coplanar or non-coplanar mode. The controller is configured to apply a limit on the field of radiation using the beam shaping apparatus, where the limit depends on whether the radiation source is in the coplanar or the non-coplanar configuration. The controller may be configured to control the beam shaping apparatus to apply the limit when the radiation source is in the at least one non-coplanar configuration, and remove the limit when the radiation source is in the coplanar configuration. For example, the controller may apply an operational rule defining a limit of retraction of at least one beam shaping member of the beam shaping apparatus 150. The limit of retraction may only be applied when the radiotherapy apparatus is in the non-coplanar mode, or retraction of one or more beam shaping member may be more limited in the non-coplanar mode.

The radiation head 104 is connected to a head actuator 130 which is configured to actuate the radiation head 104 between a coplanar configuration and one or more non-coplanar configurations. This may involve translation and/or rotation of the radiation head 104 relative to the gantry. In some implementations, the head actuator includes a curved rail along which the radiation head 104 is moved to adjust the position and angle of the radiation head 104. The controller 140 controls the configuration of the radiation head 104 via the head actuator 130.

The beam shaping apparatus 150 includes a shaping actuator 132. The shaping actuator is configured to control the position of one or more elements in the beam shaping apparatus 150 in order to shape the radiation beam 122. In some implementations, the beam shaping apparatus 150 includes an MLC and a diaphragm, and the shaping actuator 132 includes means for actuating leaves of the MLC and means for actuating blocks of the diaphragm. The controller 140 controls the beam shaping apparatus 150 via the shaping actuator 132.

Beam Shaping Apparatus

Figure 2:
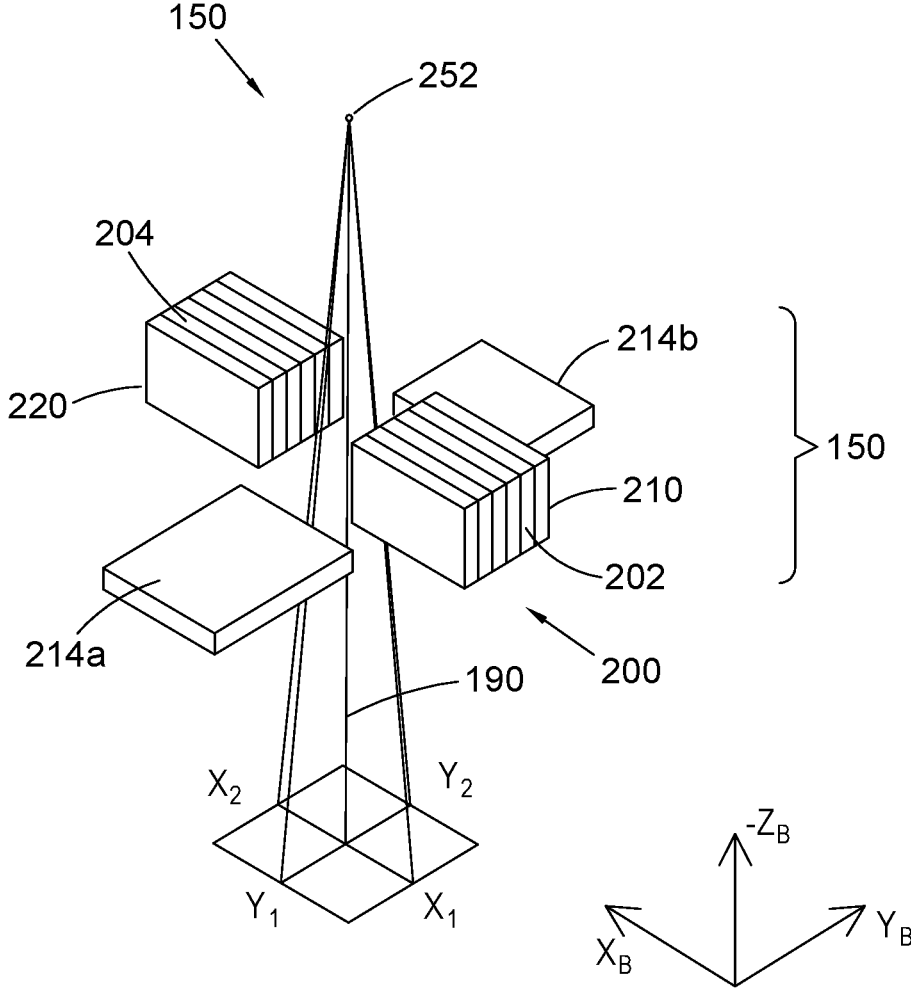
FIG. 2 depicts an example of a beam shaping apparatus.

FIG. 2 depicts an example of the beam shaping apparatus 150. FIG. 2 schematically depicts the position of a beam source 252 within the radiation source, from which radiation is produced, and schematically shows the beam passing through the beam shaping apparatus 150. The beam source 252 may be, for example, a target upon which electrons are incident to create a high-energy X-ray beam.

In the implementation depicted in FIG. 2, the beam shaping apparatus 150 includes a multi-leaf collimator, MLC, 200 and a diaphragm apparatus 214.

MLC 200 includes a plurality of elongate leaves 202, 204 oriented orthogonal to the axis of beam 122. MLC 200 includes two banks 210, 220 of leaves, forming two opposing arrays. Each leaf can be individually extended into and out of the path of radiation beam 122 in order to shape the cross-section of the beam by blocking portions thereof. The leaves are movable to provide shaping of the beam.

During radiotherapy treatment, the leaves of MLC 200 are controlled to take different positions to selectively block some or all of radiation beam 122, thereby altering the shape of the beam that reaches the patient. In other words, the MLC presents an edge to the radiation beam which can be varied so as to provide a particular beam shape.

In some implementations, beam shaping apparatus 150 includes a bank of motors, which forms part of the shaping actuator 132, with each motor configured to move a corresponding one of the leaves. Movement of each leaf by the motors is controlled by controller 140. For example, controller 140 controls leaf movement via the motors to shape radiation beam 122 for irradiating a target tissue, such as according to a treatment plan. Controller 140 moves the leaves, including advancing and retracting the leaves, by actuation of the leaf motors.

The beam shaping apparatus 150 also comprises a diaphragm apparatus. The diaphragm apparatus is configured to shape the beam of radiation, in a manner similar to the MLC 200. The diaphragm apparatus comprises one or more diaphragm blocks 214 configured to be extended into, and withdrawn from, the radiation field. In an example, the diaphragm apparatus comprises two diaphragm blocks 214a, 214b which face each other across the radiation field.

The diaphragm blocks 214a, 214b may be configured to move in a movement axis which is generally or substantially perpendicular to the beam axis, and also generally or substantially perpendicular to the movement axis of the MLC leaves. The diaphragm blocks 214a, 214b are made from a radiopaque material such as tungsten.

The beam shaping apparatus 150 further comprises diaphragm actuation means (not shown) which forms part of the shaping actuator 132. In some implementations, the diaphragm actuation means includes a diaphragm motor, which is configured to effect movement of the diaphragm blocks 214a, 214b.

Three beam directions $X_B$ $Y_B$ $Z_B$ can be defined, where the $Z_B$ direction corresponds to the beam axis 190. In coplanar mode, the beam directions $X_B$ $Y_B$ $Z_B$ correspond to the gantry directions $X_G$ $Y_G$ $Z_G$.

With reference to FIG. 2, it will be appreciated that actuation means of the MLC (e.g. the bank of motors) is configured to move the MLC leaves in the directions indicated as X1 and X2, and along a movement axis depicted in the figure as the $X_B$ direction. The diaphragm actuation means is configured to move the diaphragms in directions Y1 and Y2, and along a movement axis depicted in the figure as the $Y_B$ direction. While the diaphragm blocks 214a, 214b depicted in FIG. 2 are positioned 'underneath' the MLC (i.e. farther away from the beam source 252), in alternative implementations the diaphragm may be positioned above the MLC (e.g. closer to the beam source 252 than the MLC).

Considering the MLC, a first array 210 extends into the beam field in the $X_B$ direction from one side of the field, and the second array 220 extends into the beam field in the $X_B$ direction from the opposing side of the field. The leaves can each be moved independently to define a chosen shape between the tips of the opposing leaf banks 210, 220. Each leaf is thin in its transverse ($Y_B$) direction to provide good resolution, is deep in the $Z_B$ direction to provide adequate absorption, and long in its longitudinal ($X_B$) direction to allow it to extend across the field to a desired position.

Considering the diaphragm, movable blocks 214a and 214b adjust the width of the aperture. Specifically, the diaphragm blocks define the aperture in the $Y_B$ direction. The leaves of the MLC can be fully extended such that directly opposing leaves meet. Solely using the MLC to define the beam width would constrain the width of the aperture is to integer numbers of the width of the MLC leaves. The diaphragm blocks 214a, 214b can be moved in the $Y_B$-direction as desired, and therefore provide an unconstrained dimension of the beam width. Further, the tips of the leaves of the MLC can be curved and there may be some degree of leakage between the tips of directly opposing MLC leaves from opposing banks 210, 220 when fully extended to close off parts of the field. The diaphragm blocks 214a, 214b absorb radiation outside the desired width of the aperture to reduce leakage of the beam in locations outside the aperture.

Coplanar and Non-Coplanar Modes

Figures 3A, 3B:
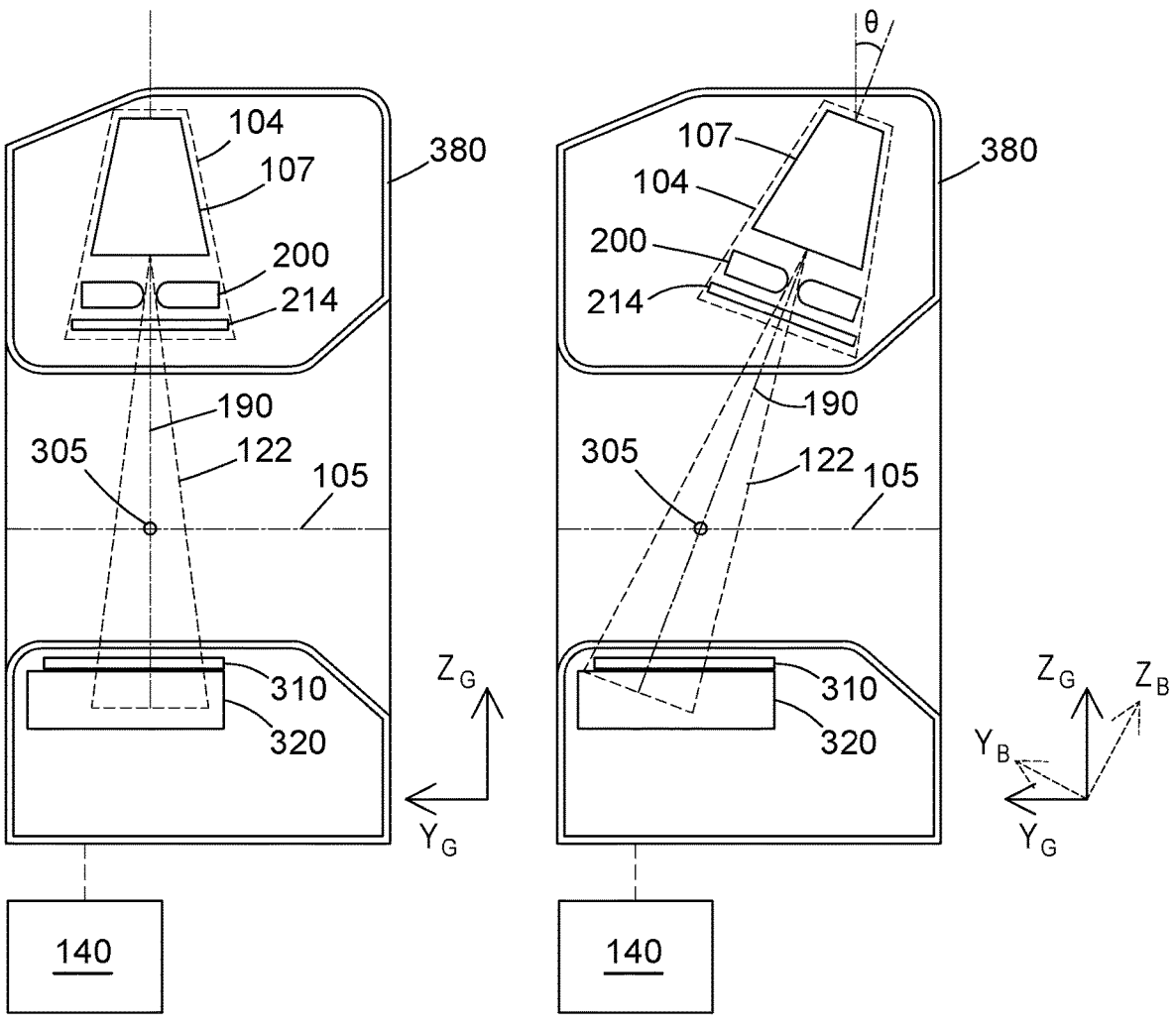
FIGS. 3A and 3B illustrate simplified sections through the radiotherapy apparatus.

FIGS. 3A and 3B illustrate simplified sections through the radiotherapy apparatus 100. FIG. 3A illustrates the radiotherapy apparatus in a coplanar mode, while FIG. 3B illustrates the radiotherapy apparatus in a non-coplanar (or tilted) mode.

As shown in FIGS. 3A and 3B, the radiation head 104 emits a radiation beam 122 along a beam axis 190 (or radiation axis or beam path). The radiation beam 122 is incident on a beam receiving apparatus which includes a beam stopper 320 and a radiation detector 310. The radiation detector 310 may comprise, for example, and electronic portal imaging device (EPID). The beam 122 is shaped using a beam shaping apparatus comprising an MLC 200 and a diaphragm 214. The beam axis 190 intersects the axis of rotation 105 at or near the isocentre 305. As shown in FIGS. 3A and 3B, the beam axis 190 can pass through the isocentre in both coplanar and non-coplanar modes.

In the coplanar mode of FIG. 3A, the beam directions $X_B$ $Y_B$ $Z_B$ correspond to the gantry directions $X_G$ $Y_G$ $Z_G$.

The radiation head 104 comprising the radiation source 107 and the beam shaping apparatus 150 may be disposed within a housing 380. The housing provides protection and also means that coplanar and non-coplanar treatment can be provided without movement of the radiation head 104 being visible for user or patient, and without any risk of inadvertent contact between the subject and the radiation head 104 (or the beam receiving apparatus 106).

In the non-coplanar mode of FIG. 3B, the radiation head 104 is in a different position and orientation compared to the coplanar mode of FIG. 3A. Compared to the coplanar mode, in the non-coplanar mode the radiation head is both tilted (e.g. rotated) and translated relative to the gantry. However, the beam receiving apparatus 106 may remain in the same relative position in both the coplanar and the non-coplanar modes. As shown in FIGS. 3A and 3B, the radiotherapy apparatus 100 provides movement of the radiation head 104 in the $Y_G$ $Z_G$ plane (in addition to the rotational movement around the axis of rotation 105 provided by the gantry).

As shown in FIG. 3B, in the non-coplanar mode, the beam directions $X_B$ $Y_B$ $Z_B$ do not correspond to the gantry directions $X_G$ $Y_G$ $Z_G$. The $Y_B$ $Z_B$ directions are rotated relative to the $Y_G$ $Z_G$ directions by an angle θ, corresponding to the change in the angle of the radiation source 107.

The controller 140 controls movement of the radiation head 104 to rotate the beam in the $Y_G$ $Z_G$ plane (e.g. tilted with respect to the patient longitudinal axis, while preferably keeping the isocentre in the same position) and also controls the beam shaping apparatus to limit the field of the beam in the $Y_G$ direction. This helps to improve the amount of the radiation emitted by the radiation head which is incident on the beam receiving apparatus, for example to reduce the amount of radiation emitted by the radiation head which is not incident on the beam receiving apparatus.

Due to the operation of the controller 140 and beam shaping apparatus 150 to shape the field of radiation, it is not necessary for the radiotherapy apparatus 100 to provide movement of the beam receiving apparatus 106 in the $Y_G$ $Z_G$ plane. In some embodiments, the beam receiving apparatus 106 may remain stationary (e.g. fixed), or the beam receiving apparatus 106 may be moved through a smaller range of motion than that of the radiation head 104. This means that the radiotherapy apparatus 100 can be made smaller, and with fewer moving components, which increases reliability and reduces costs.

The radiation head 104 is moved between the coplanar configuration and the non-coplanar configuration by the head actuator (not shown for simplicity). This can be realised in many different ways that would be apparent to the skilled person. For example, this could be carried out using a motor with a cog-wheel that travels along a toothed curved rail, or by using a ball screw with a ball nut. In some implementations, the radiation head is moved between two fixed positions, for example with orientations at 0 and 25 degrees for the coplanar and non-coplanar configurations respectively. For example, in the coplanar configuration the radiation head 104 is orientated such that the beam axis 190

(and radiation source 107) is perpendicular to the axis of rotation 105. At this position the radiation source 107 is considered to be at 0 degrees. In the non-coplanar configuration, the radiation head 104 is orientated such that the radiation source 107 is at a different (e.g. non-zero) angle (e.g. 25 degrees to the coplanar radiation source 107, and 65 degrees to the axis of rotation 105). As shown in FIG. 3B, the angle θ is the angle of the radiation source 107 in non-coplanar mode compared to the angle of the radiation source 107 in coplanar mode.

In the non-coplanar mode, the distance from the beam source to the isocentre is greater than in the coplanar mode. In some implementations, this distance is 92 cm in coplanar mode, and 100 cm in non-coplanar mode. This advantageously means the bore of the radiotherapy apparatus can be kept as large as possible. It also helps to keep the rotational moment of inertia of the gantry the same (or at least the change in the rotational moment of inertia between modes is minimised). This is because the rotational moment of inertia of the radiation head depends on its distance from the axis of rotation. In some implementations, the centre of mass of the radiation head remains the same distance from the axis of rotation in both coplanar and non-coplanar modes. Minimising change in the rotational moment of inertia of the gantry can help avoid, for example, complicated counterweight systems.

In the coplanar configuration, the radiation head 104 is configured to rotate in a first plane of rotation, e.g. a first sagittal plane. This first plane of rotation passes through the isocentre 305. The radiation head 104 is positioned such that the beam axis 190 is coplanar with the first plane of rotation.

In the non-coplanar configuration, the radiation head 104 is positioned to rotate in a respective second plane of rotation which is parallel to and displaced from the first plane of rotation, e.g. a second sagittal plane displaced from the first plane by a distance in the y direction. In this configuration, the second plane of rotation is also displaced from the isocentre 305.

As stated above, the controller 140 controls the configuration of the radiation head 104 via the head actuator 130. The controller 140 controls the MLC 200 via the shaping actuator 132. The controller 140 controls the MLC (and/or the diaphragm) to reduce the spread of the field of radiation when the radiotherapy apparatus is in the non-coplanar mode. The spread of the field (e.g. defined by a limit of retraction) is reduced by an amount that improves the amount of radiation of the field of radiation that is incident on the radiation detector 310 and/or the beam stopper 320, e.g. to ensure that all of the field is incident on the radiation detector 310 and the beam stopper 320. In many implementations, this is done by closing off outer edge leaves in the MLC 200.

As shown in FIGS. 3A and 3B, the beam 122 is incident on the radiation detector 310 and the beam stopper 320 in both the coplanar and non-coplanar modes. Therefore, advantageously, there is no need to provide a separate radiation detector and/or beam stopper (or other beam receiving apparatus) for the two modes. Additionally, in some embodiments, there is no need to provide additional movement of the beam receiving apparatus. For example, the radiation detector 310 and the beam stopper 320 can be fixed to the rotating gantry 102. Also, the size of the radiation detector and/or beam stopper can be made smaller, which in turns allows the size of the radiotherapy apparatus as a whole to be reduced, taking up less floor space. In some embodiments, the beam receiving apparatus may still be moved, although it is not necessary to move the beam receiving apparatus through the same distance as the radiation head.

The controller may use signals from the radiation detector in order to determine the spread of the radiation field, and the controller may reduce the spread of the field as it detects that the field is approaching the edge of the radiation detector. That is, the controller may be further configured to determine a spread of the radiation field using signals from the radiation detector. If the determined spread of the radiation field is within a threshold distance from the edge of the radiation detector, then the beam shaping apparatus may be controlled to reduce the spread of the radiation field.

MLC Operation

Figure 4A:
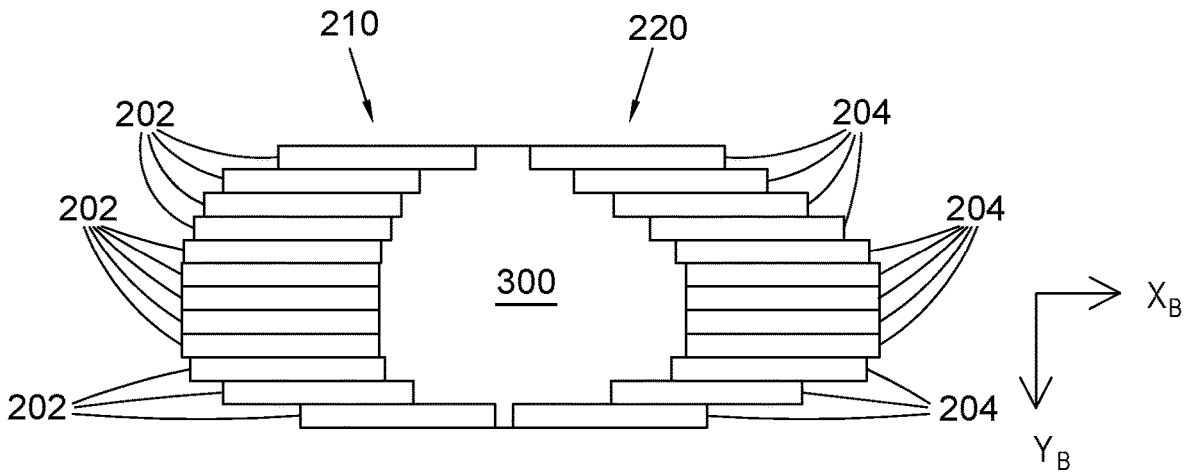
FIGS. 4A and 4B are top plan views of a leaf array in a first implementation.
Figure 4B:
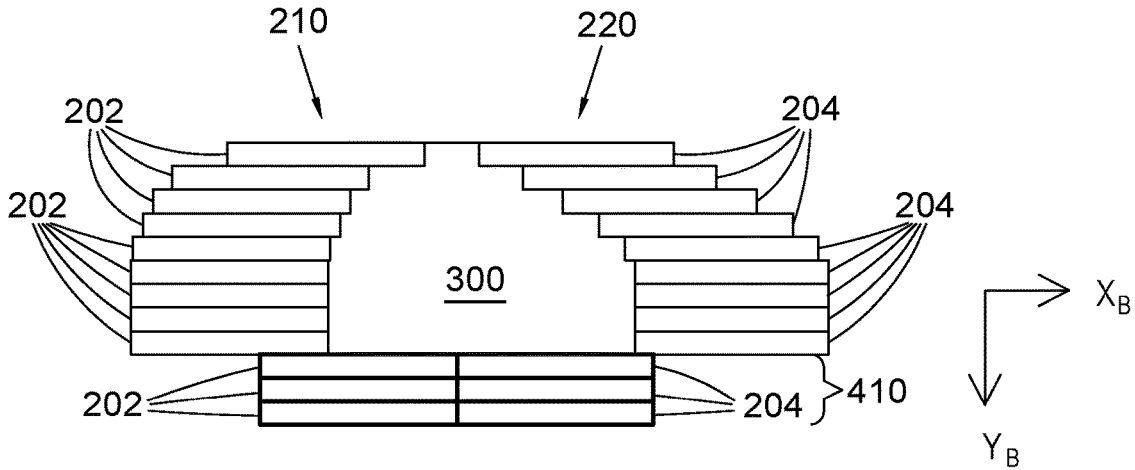

FIGS. 4A and 4B show a leaf array of the MLC 200, in an implementation of the present disclosure in which the MLC has a first orientation with respect to the patient longitudinal axis. FIGS. 4A and 4B show arrangements of the MLC leaves 202, 204 when the radiotherapy apparatus 100 is in the coplanar and non-coplanar modes respectively. FIG. 4A shows an arrangement of the leaves when the radiotherapy apparatus 100 is in the coplanar mode, while FIG. 4B shows an arrangement of the leaves when the radiotherapy apparatus is in the non-coplanar mode.

MLC 200 includes two banks 210, 220 of leaves, each leaf of which can be individually extended into and out from the path of the radiation beam 122 so that their respective tips shape the cross-section of the beam by blocking portions thereof. The controller 140 controls placement of the leaf tips 206 to shape the radiation beam 122, defining an aperture 300 through which the radiation beam 122 can pass, thereby shaping the beam for irradiating a target tissue according to a treatment plan.

The plurality of leaves 202, 204 are oriented orthogonal to the axis of beam 122, which in the view of FIGS. 4A and 4B is travelling in a direction into the page. In this implementation, the MLC is oriented such that the leaves move back and forth in the x direction.

FIG. 4A shows the MLC 200 when the radiotherapy apparatus is in the coplanar mode, in which the leaves have their normal freedom of movement back and forth in the x direction.

On the other hand, FIG. 4B shows the MLC 200 when the radiotherapy apparatus is in the non-coplanar mode, in which the field of radiation has been limited in the $Y_B$ direction. This is done by the controller 140 controlling one or more of the leaves of the MLC to block radiation furthest along the $Y_B$ axis.

Generally, the controller is configured to control the beam shaping apparatus to prevent the field of radiation from extending beyond a defined threshold in the y (or x) direction as the beam axis moves in the y (or x) direction. The part of the field which is reduced is generally on an opposite side to the direction in which the radiation head 104 is moved in order to reach the non-coplanar configuration.

The controller may be configured to control the position of one or more leaves of the MLC based on whether the radiation source is in the coplanar or non-coplanar configuration. For example, the controller may set a limit of retraction a leaf based on whether the radiation source is in the coplanar or non-coplanar configuration.

When the radiotherapy apparatus is configured to deliver radiation in the non-coplanar mode, one or more leaves of the MLC may be subject to at least one additional operational rule. One, or a plurality of adjacent, leaves are restrained leaves 410. The purpose of restraining these leaves 410 is to block the portion of the radiation beam which would otherwise have passed beyond the beam receiving apparatus. In an example, the one or more restrained leaves 410 may have a limit of retraction imposed upon them. The limit of retraction may be that the one or more restrained leaves 410 may not retract from their maximum extension into the radiation field.

Turning to the specific implementation depicted in FIG. 4B, in this case three of the outermost leaves in each of leaf banks 210, 220, are positioned to extend into the field such that there is substantially no gap between opposing leaves (e.g. the leaf pairs are fully closed). This means that the radiation field at these outermost leaves is blocked, thereby limiting the spread of the radiation field. This prevents any of the field from extending beyond the beam receiving apparatus when the radiotherapy apparatus is in the non-coplanar mode.

In some implementations, the closed leaves have a retraction limit set to 0 by the controller, meaning they are fully extended into the centre of the field. In some implementations, leaves 202, 204 are configured to be extended into the path of radiation beam 122 to a location beyond a halfway point between leaf banks 210, 220, allowing the leaves 202, 204 to be fully closed together where their tips can meet at any point (not just the halfway point).

The controller 140 may calculate a retraction limit of MLC leaves based on the amount of beam limitation needed in the $Y_B$ direction to provide appropriate limiting of the beam in the $Y_G$ direction (e.g. the direction of the longitudinal axis of the patient) such that all, or substantially all, radiation is incident on the beam receiving apparatus. This calculation depends on the angle of tilt θ.

Figure 5A:
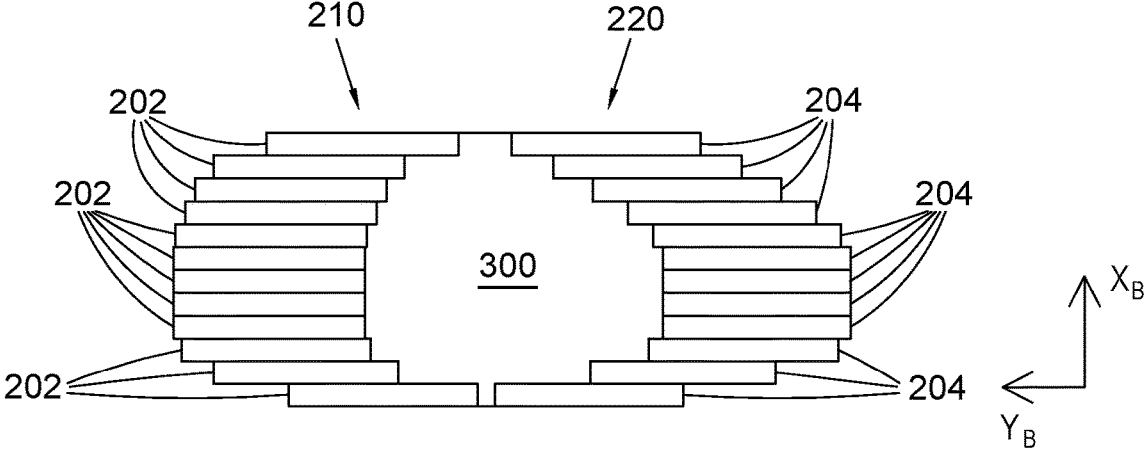
FIGS. 5A and 5B are top plan views of a leaf array in a second implementation.
Figure 5B:
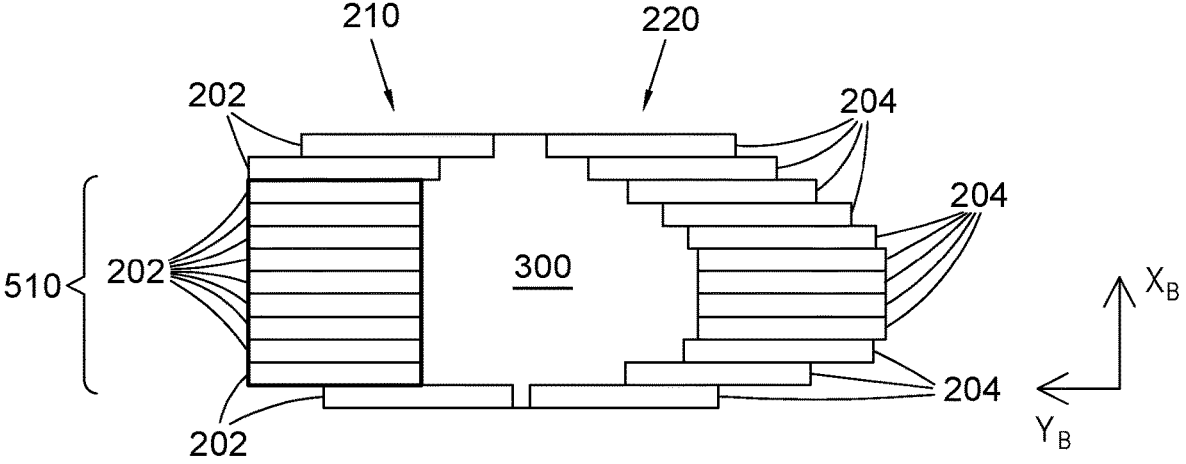

FIGS. 5A and 5B show a leaf array of the MLC 200 in an implementation of the present disclosure in which the MLC has a second, different orientation with respect to the patient longitudinal axis. FIG. 5A shows an arrangement of the leaves when the radiotherapy apparatus 100 is in the coplanar mode, while FIG. 5B shows an arrangement of the leaves when the radiotherapy apparatus is in the non-coplanar mode. In this implementation, the MLC (which may be rotatable) is oriented such that the leaves move back and forth in the y direction.

FIG. 5A shows the MLC 200 when the radiotherapy apparatus is in the coplanar mode, in which the leaves have their normal freedom of movement back and forth in the y direction.

On the other hand, FIG. 5B shows the MLC 200 when the radiotherapy apparatus is in the non-coplanar mode, in which the field of radiation has been limited in in the x direction. This is done by the controller 140 controlling one or more of the leaves of the MLC to block radiation furthest along the y axis. For example, the controller may set a retraction limit of all the leaves in a leaf block, in order to ensure radiation is blocked from paths which are not incident on the beam receiving apparatus.

As described above in relation to FIGS. 4A and 4B, when the radiotherapy apparatus is configured to deliver radiation in the non-coplanar mode, one or more leaves of the MLC may be subject to at least one additional operational rule. One, or a plurality of adjacent, leaves are restrained leaves 510. The purpose of restraining these leaves 510 is to block the portion of the radiation beam which would otherwise have passed beyond the beam receiving apparatus. In an example, the one or more restrained leaves 510 may have a limit of retraction imposed upon them. The limit of retraction may be that the one or more restrained leaves 510 may not retract beyond a particular value. In other words, the restrained leaves 510, which in some implementations may be the leaves of an entire leaf bank, may be prevented from retracting beyond a particular value.

As can be seen in FIG. 5B, the controller 140 controls the leaves 202 of one leaf bank 210 to reduce their maximum retraction out of the radiation field. A plurality of the leaves 510 have reached their maximum retraction out of the field and are therefore located in the same longitudinal position. This means that the radiation field at these leaves is blocked, thereby limiting the spread of the radiation field. This prevents any of the field from extending beyond the beam receiving apparatus when the radiotherapy apparatus is in the non-coplanar mode.

Diaphragm Operation

It will be appreciated that movement of the diaphragm may be controlled based on whether the radiotherapy apparatus is in the coplanar or non-coplanar modes—alternatively or in addition to controlling the MLC in this way. When the radiotherapy apparatus is configured to deliver radiation in the non-coplanar mode, one or more blocks of the diaphragm may be subject to at least one additional operational rule. In an example, the one or more diaphragm blocks may have a limit of retraction imposed upon them. The limit of retraction may be that the one of the diaphragm blocks may not retract beyond a certain position, to limit one side of the field of radiation.

Guide Rails

Figure 6A:
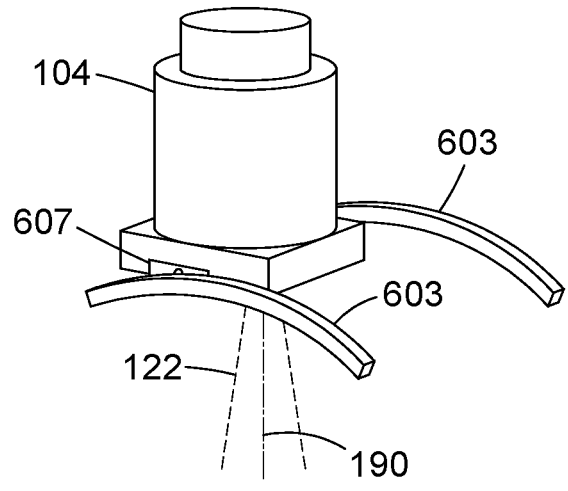
FIGS. 6A and 6B illustrate an implementation of a head actuator.
Figure 6B:
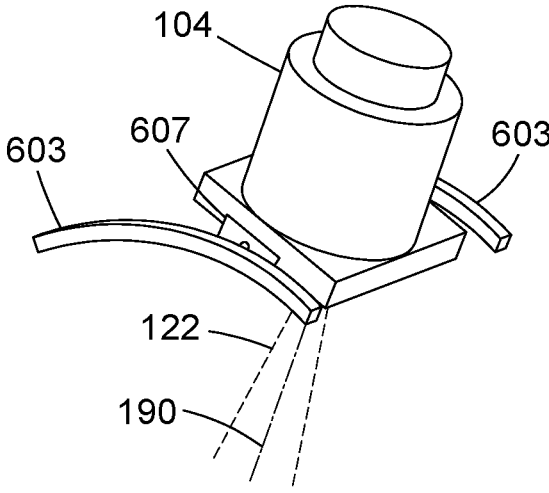

FIGS. 6A and 6B illustrate an implementation in which the head actuator 130 is provided by two curved guide rails 603 which support the radiation head 104. FIG. 6A shows the radiation head 104 in the coplanar configuration, while FIG. 6B shows the radiation head 104 in the non-coplanar configuration.

The radiation head 104 is movably mounted to the guide rails 603 via two supports 607. The radiation head 104 can be translated along the guide rails 603, and due to the curve of the guide rails the orientation of the radiation head 104 changes as it moves on the rails. This changes the angle of the radiation beam 122 which is emitted by the radiation head 104.

In some implementations, the radiation head 104 is configured to move between two fixed positions in which a first position corresponds to the coplanar configuration and a second position corresponds to the non-coplanar configuration. For example, in the second position the radiation head 104 may be tilted by 25 degrees compared to the first position. Advantageously, only providing two positions makes it safer and easier to produce treatment plans because a degree of freedom is removed. This can make it easier to get regulatory approval too since the harmful beam of radiation is limited in its directionality compared to a freely moving source.

In some implementations, in the coplanar position on the guide rails the radiation head 104 emits beam 122 in a direction in which the beam axis 190 is perpendicular to the axis of rotation of the gantry. On the other hand, when the radiation head 104 is in the non-coplanar position on the guide rails, the radiation head 104 emits beam 122 in a direction in which the beam axis 190 is non-perpendicular to the axis of rotation of the gantry.

The radiation head 104 is connected to a head actuator 130 which is configured to actuate the radiation head 104 between a coplanar configuration and one or more non-coplanar configurations. In some implementations, the head actuator moves the radiation head 104 along a curved rail to adjust the position and angle of the head 104. The controller 140 controls the configuration of the radiation head 104 via the head actuator 130.

The guide rails 603 and supports 607 are configured to tilt the radiation head as it moves laterally. The tilt is provided by the curve of the guide rails 603 and also due to rotation of the radiation head relative to the guide rail.

Modifications and Alternatives

Any implementations, examples and embodiments described herein can be combined.

Overview—Radiotherapy Apparatus

The source of radiation 107 may comprise a heavy metal target toward which high energy electrons are directed. When the electrons strike the target, X-rays are produced in a variety of directions. A primary collimator (not shown) may block X-rays travelling in certain directions and pass only forward travelling X-rays to produce a treatment beam. The X-rays may be filtered and may pass through one or more ion chambers for dose measuring. In some implementations, the source of radiation 107 is configured to emit either an X-ray beam or a particle beam. Such implementations allow the apparatus to provide particle beam therapy, i.e. a type of external beam therapy where particles (e.g. protons or light ions), rather than X-rays, are directed toward the target region.

In some examples, the radiation source 107 and the beam shaping apparatus 150 are provided as a single unit, or alternatively the radiation source 107 and the beam shaping apparatus 150 may be provided separately.

It will be appreciated that the gantry may be replaced with one or more apparatus which allows the radiation source, the beam shaping apparatus and the beam receiving apparatus to rotate around an axis of rotation.

The beam shaping apparatus is described as including a combination of a diaphragm and an MLC. However, the beam shaping apparatus may include only a diaphragm or only an MLC, or neither. The diaphragm can include any combination of blocks, for example only two blocks which define the aperture in the x direction or only two blocks which define the aperture in the y direction.

The beam shaping apparatus may be configured to reduce the spread of the field of radiation in the at least one non-coplanar configuration in comparison to the coplanar configuration. Where the beam shaping apparatus comprises a multi-leaf collimator, a position of at least one leaf of the MLC may be dependent on whether the radiation source is in the coplanar or non-coplanar configuration.

As described herein, the radiotherapy apparatus 100 may include a radiation detector. The radiation detector is suitable for, and configured to, produce radiation intensity data. In particular, the radiation detector is positioned and configured to detect the intensity of radiation which has passed through the subject. The radiation detector may also be described as radiation detecting means, and may form part of a portal imaging system.

Multiple different non-coplanar configurations may be provided, where the beam of radiation is emitted at multiple different angles, and the controller configured to control the beam limiting apparatus to limit the beam as described herein in each of the multiple different non-coplanar configurations.

Beam Shaping Apparatus

The beam shaping apparatus 150 may comprises an interface ring or other means which is configured to allow the beam shaping apparatus 150 to be attached to the radiation source or other components, for example an ion chamber and/or dosimeter.

In some implementations, the MLC 200 also includes leaf bank actuation means which forms part of the shaping actuator 132. The leaf bank actuation means is configured to move the entire bank of leaves such that the bank of leaves may be extended into, and withdrawn from, the radiation field. Once the banks are in the correct position, each leaf is individually actuated so as to form the desired shape.

The shaping actuator may comprise leaf motors and/or an arrangement of lead screws. Alternatively or in addition, the shaping actuator may include any actuator or combination or actuators for controlling the leaves of the MLC and/or the diaphragm blocks.

It is noted that, while it is described herein that the diaphragm blocks define the aperture in the x direction, the diaphragm blocks may instead define the aperture in the y direction (additionally or alternatively to the MLC). The diaphragm may include two pairs of blocks in order to define the aperture in the x and y directions.

Coplanar and Non-Coplanar Modes

In some implementations, the radiation head is not disposed within a housing.

In some implementations, the rotation of the radiation head is a rotation about an axis which is perpendicular to both the beam axis 190 and the axis of rotation of the gantry, and which intersects these axes at the isocentre. In this case, the distance from beam source to isocentre (and/or axis of rotation) is the same for both the coplanar and the non-coplanar modes.

In many implementations, when the radiotherapy apparatus is in the non-coplanar mode the radiation beam is emitted at a fixed angle—for example where the beam axis is at 75 degrees to the axis of rotation of the radiation head. In these implementations, the treatment plan can include a non-coplanar adjustment which causes the radiation field to be limited in a predefined manner. For example, the movement of certain leaves of the MLC can be limited. Also, the MLC can be prevented from rotating relative to the radiation source.

In some implementations, the MLC can be rotatable around the beam axis in coplanar configuration but fixed in a transverse direction when in the non-coplanar configuration, e.g. in the non-coplanar configuration the MLC leaves may only limit the beam in the y direction. In some implementations, the MLC 32 does not rotate around the beam axis.

In some embodiments, only one guide rail may be provided. The radiotherapy apparatus may be configured to place the radiation head more than one tilted position—for example it can be held in a plurality of predefined positions along the guide rail(s). The radiation head may be prevented from emitting a beam in between positions, such that beams can only be emitted on one or more predefined positions.

Reference has primarily been made herein to an apparatus capable of delivering radiation from a coplanar mode and a single non-coplanar mode. However, apparatuses according to the present disclosure may comprise a plurality of non-coplanar modes. In other words, multiple tilt angles between the radiation source and a plane perpendicular to the patient longitudinal axis may be provided. In such implementations, different operational rules apply for the beam shaping apparatus depending on the mode of radiation delivery. As will be appreciated upon reference to FIGS. 3a, 3b, and 4a and 4b, as the tilt angle θ of a non-coplanar mode increases, the less of the radiation field is incident upon the beam stopper and/or detector. Accordingly, for an apparatus comprising multiple non-coplanar modes of radiation delivery, each non-coplanar mode may have an associated number of MLC leaves upon which a limit of retraction is imposed. For an implementation in which the MLC is oriented in the manner depicted in FIGS. 4a, 4b, successively more leaves may form part of the restrained leaves 410 as the tilt angle θ increases. For an implementation in which the MLC is oriented in the manner depicted in FIGS. 5a, 5b, a successively greater retraction limit may be imposed on the restrained leaves 510 as the tilt angle θ increases such that the restrained leaves 510 are constrained to be extended further and further into the radiation field.

In many embodiments, the beam axis 190 is aligned with a central axis of the radiation source. As noted previously, the angle at which the field of radiation is directed by the radiation head is defined by the beam axis 190. The radiation beam axis 190 may be, for example, a centre of the radiation beam 122 or a point of maximum intensity. The central axis of the radiation source may be defined as, for example, a line joining the beam source to the operational centre of the beam shaping apparatus 150 (e.g. centre of the MLC), and/or defined as an axis of rotation of the beam shaping apparatus 150.

In some embodiments, the angle of the field of radiation (e.g. the beam axis) may be further adjusted using the beam shaping apparatus 150. The beam axis 190 need not be aligned with the central axis of the radiation source when the angle of the field of radiation is adjusted in this manner. This may involve applying at least one additional operational rule defining further adjustments to the beam shaping apparatus.

Adjusting the beam shaping apparatus can change the angle of the beam axis 190 relative to the central axis of the radiation source because the beam source 252 produces divergent rays of radiation. For example, applying a translational movement to the aperture defined by the beam shaping apparatus can result in radiation emitted at a different angle from the beam source 252 passing through the aperture. A translational movement can be defined as, for example, moving the aperture in its entirety in a particular direction. This may involve translating the aperture defined by the leaves of the MLC in a direction (e.g. by moving all MLC leaves by 50 mm in the X direction) which will result in radiation emitted at a different angle from the beam source 252 to pass through the aperture of the MLC. Thus, an additional operational rule defining such an adjustment to the beam shaping apparatus can be implemented to further adjust the angle of the field of radiation.

The adjustment of the angle of the field of radiation can be carried out when the radiation source is configured in the non-coplanar configuration (or the coplanar configuration), without further movement/tilting of the radiation source itself, but instead using the beam shaping apparatus. For example, this may involve using the controller 140 to control the beam shaping apparatus 150, and may involve using the shaping actuator 132 to direct the beam shaping apparatus in such a manner as to alter or modify the angle θ.

For example, the beam shaping apparatus may comprise a multi-leaf collimator MLC 200. The MLC 200 comprises a plurality of leaves 202, 204, whose movements can be controlled by the controller 140 based on whether the radiation source is in the coplanar or non-coplanar configuration. The leaves of the MLC 200 are controlled to take different positions to selectively block some or all of the radiation beam 122, thereby altering the shape of the beam 122. In these embodiments, the leaves 202, 204 of the multi-leaf collimator 200 may be further configured such that one or more individual leaves can undergo translational movement in such a manner as to tilt the angle of the radiation field in a desired direction. This may involve applying at least one additional operational rule defining a translational motion of one or more leaves.

Preferably, the operational rule defining the limit of retraction is given precedence over any additional operational rule further modifying the beam angle using the beam shaping apparatus. This is to ensure that the radiation field is incident only upon the beam stopper and/or detector in the case where more than one operational rule has been implemented.

In embodiments where a further adjustment to the direction of the radiation field may cause the radiation field to no longer be fully incident on the beam stopper and/or detector, the implementation of a further operational rule which would adjust the direction of the field in such a manner is forbidden. On the other hand, if it is possible to apply one or more further operational rules defining a further adjustment of the radiation field where the radiation remains fully incident upon the beam stopper and/or detector after the rule has been applied, the implementation of one or more further operational rules is not forbidden. Examples of this are described below.

The adjustment of the beam shaping apparatus 150 can be used to further increase the angle of the radiation field when the radiation source is in the non-coplanar configuration. For example, if the radiation head 104 were at a non-zero angle of $\theta^*$, the beam shaping apparatus 150 could be adjusted to give a further tilt of a to the beam, giving a total angle of the beam $\theta=\theta^*+\alpha$. This can be advantageous in cases where the tilting of the radiation head 104 is limited, and further shaping of the beam is needed to increase or change the angle of the field of radiation. This may also be advantageous in instances where tilt of the radiation head alone (when in the non-coplanar configuration) is not sufficient to cause the field of radiation to be incident on the a beam stopper/detector. In these examples, the beam shaping apparatus can be used to further increase the tilt angle of the field of radiation beyond the tilt angle of the radiation head so as to ensure the radiation is incident on the beam stopper/detector.

In another implementation of the apparatus, the beam shaping apparatus 150 can be used to adjust or modify the angle $\theta$ of the radiation field to allow for intermediate angles between the coplanar mode and at least one non-coplanar mode to be realised. This can be advantageous in cases where there are a limited number of non-coplanar modes (e.g. just one), as it allows for further angles of the radiation field to be realised.

The controller is a computing device, computer, processor, or other processing apparatus. The controller may be formed by several discrete processors.

Figure 7:
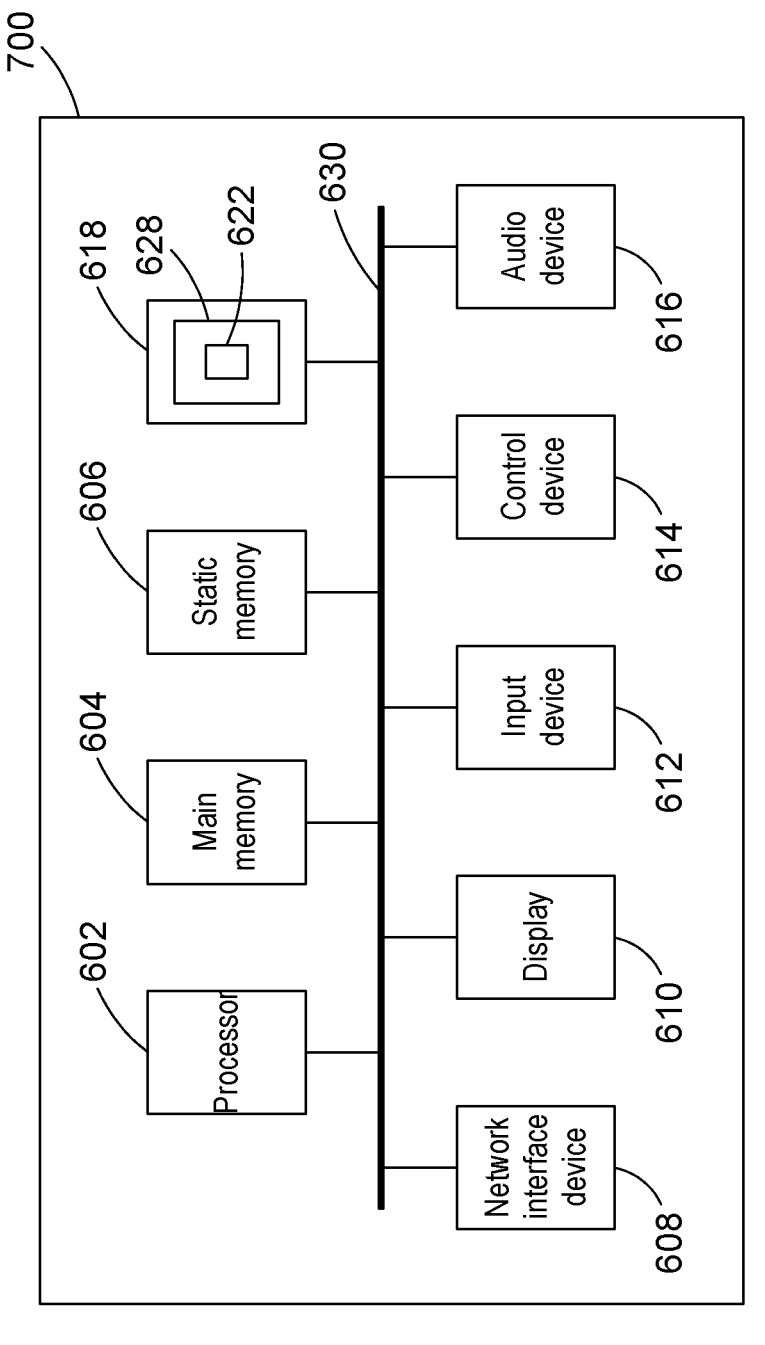
FIG. 7 depicts a block diagram of one implementation of a computing device according to the present disclosure.

FIG. 7 is a block diagram of one implementation of a computing device 700 within which a set of instructions, for causing the computing device to perform any one or more of the methodologies discussed herein, may be executed. In alternative implementations, the computing device may be connected (e.g., networked) to other machines in a Local Area Network (LAN), an intranet, an extranet, or the Internet. The computing device may operate in the capacity of a server or a client machine in a client-server network environment, or as a peer machine in a peer-to-peer (or distributed) network environment. The computing device may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single computing device is illustrated, the term "computing device" shall also be taken to include any collection of machines (e.g., computers) that individually or jointly execute a set (or multiple sets) of instructions to perform any one or more of the methodologies discussed herein.

The example computing device 700 includes a processing device 602, a main memory 604 (e.g., read-only memory (ROM), flash memory, dynamic random access memory (DRAM) such as synchronous DRAM (SDRAM) or Rambus DRAM (RDRAM), etc.), a static memory 606 (e.g., flash memory, static random access memory (SRAM), etc.), and a secondary memory (e.g., a data storage device 618), which communicate with each other via a bus 630.

Processing device 602 represents one or more general-purpose processors such as a microprocessor, central processing unit, or the like. More particularly, the processing device 602 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 602 may also be one or more special-purpose processing devices such as an application specific integrated circuit (ASIC), a field programmable gate array (FPGA), a digital signal processor (DSP), network processor, or the like. Processing device 602 is configured to execute the processing logic (instructions 622) for performing the operations and steps discussed herein.

The computing device 700 may further include a network interface device 608. The computing device 700 also may include a video display unit 610 (e.g., a liquid crystal display (LCD) or a cathode ray tube (CRT)), an alphanumeric input device 612 (e.g., a keyboard or touchscreen), a cursor control device 614 (e.g., a mouse or touchscreen), and an audio device 616 (e.g., a speaker).

The data storage device 618 may include one or more machine-readable storage media (or more specifically one or more non-transitory computer-readable storage media) 628 on which is stored one or more sets of instructions 622 embodying any one or more of the methodologies or functions described herein. The instructions 622 may also reside, completely or at least partially, within the main memory 604 and/or within the processing device 602 during execution thereof by the computer system 700, the main memory 604 and the processing device 602 also constituting computer-readable storage media.

The various methods described above may be implemented by a computer program. The computer program may include computer code arranged to instruct a computer to perform the functions of one or more of the various methods described above. The computer program and/or the code for performing such methods may be provided to an apparatus, such as a computer, on one or more computer readable media or, more generally, a computer program product. The computer readable media may be transitory or non-transitory. The one or more computer readable media could be, for example, an electronic, magnetic, optical, electromagnetic, infrared, or semiconductor system, or a propagation medium for data transmission, for example for downloading the code over the Internet. Alternatively, the one or more computer readable media could take the form of one or more physical computer readable media such as semiconductor or solid state memory, magnetic tape, a removable computer diskette, a random access memory (RAM), a read-only memory (ROM), a rigid magnetic disc, and an optical disk, such as a CD-ROM, CD-R/W or DVD.

In an implementation, the modules, components and other features described herein can be implemented as discrete components or integrated in the functionality of hardware components such as ASICS, FPGAs, DSPs or similar devices.

A "hardware component" is a tangible (e.g., non-transitory) physical component (e.g., a set of one or more processors) capable of performing certain operations and may be configured or arranged in a certain physical manner. A hardware component may include dedicated circuitry or logic that is permanently configured to perform certain operations. A hardware component may be or include a special-purpose processor, such as a field programmable gate array (FPGA) or an ASIC. A hardware component may also include programmable logic or circuitry that is temporarily configured by software to perform certain operations.

Accordingly, the phrase "hardware component" should be understood to encompass a tangible entity that may be physically constructed, permanently configured (e.g., hardwired), or temporarily configured (e.g., programmed) to operate in a certain manner or to perform certain operations described herein.

In addition, the modules and components can be implemented as firmware or functional circuitry within hardware devices. Further, the modules and components can be implemented in any combination of hardware devices and software components, or only in software (e.g., code stored or otherwise embodied in a machine-readable medium or in a transmission medium).

Unless specifically stated otherwise, as apparent from the following discussion, it is appreciated that throughout the description, discussions utilizing terms such as "controlling", "receiving", "determining", "comparing", "enabling", "maintaining," "identifying," "applying," "transmitting," "generating," or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The approaches described herein may be embodied on a computer-readable medium, which may be a non-transitory computer-readable medium. The computer-readable medium may carry computer-readable instructions arranged for execution upon a processor so as to cause the processor to carry out any or all of the methods described herein.

The term "computer-readable medium" as used herein refers to any medium that stores data and/or instructions for causing a processor to operate in a specific manner. Such storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, or any other magnetic data storage medium, a CD-ROM, any other optical data storage medium, any physical medium with one or more patterns of holes, a RAM, a PROM, an EPROM, a FLASH-EPROM, NVRAM, and any other memory chip or cartridge.

It is to be understood that the above description is intended to be illustrative, and not restrictive. Many other implementations will be apparent to those of skill in the art upon reading and understanding the above description. Although the present disclosure has been described with reference to specific example implementations, it will be recognised that the disclosure is not limited to the implementations described, but can be practiced with modification and alteration within the scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

The invention claimed is:

1. A radiotherapy apparatus comprising:
a radiation source;
a beam shaping apparatus;
a rotatable gantry configured to rotate about a rotation axis;
a beam receiving apparatus; and
a controller configured to control the beam shaping apparatus, wherein:
the radiation source is configured to deliver radiation in each of a coplanar configuration and at least one non-coplanar, tilted, configuration;
in the coplanar configuration, the radiation source is positioned to rotate about the rotation axis and to rotate in a first plane;
in the at least one non-coplanar, tilted, configuration, the radiation source is non-coplanar with respect to the first plane such that a field of radiation produced by the radiation source is directed at an oblique angle relative to the first plane and the rotation axis;
in the at least one non-coplanar, tilted, configuration, the radiation source is positioned to rotate in a respective second plane parallel to and displaced from the first plane;
the beam receiving apparatus remains in the same place relative to the rotatable gantry when the radiation source is in the coplanar configuration or the at least one non-coplanar, tilted, configuration;
the beam shaping apparatus is configured to direct the radiation produced by the radiation source towards the beam receiving apparatus in each of the coplanar configuration and the at least one non-coplanar, tilted, configuration; and
the controller is configured to:
control the beam shaping apparatus to apply a limit on the field of radiation produced by the radiation source based on whether the radiation source is configured in the coplanar configuration or the at least one non-coplanar, tilted, configuration;
apply the limit when the radiation source is in the at least one non-coplanar, tilted, configuration to prevent the field of radiation from extending beyond the beam receiving apparatus; and
remove the limit when the radiation source is in the coplanar configuration.

2. The radiotherapy apparatus of claim 1, wherein the beam receiving apparatus comprises at least one of a beam stopper or a radiation detector.

3. The radiotherapy apparatus of claim 2, wherein the controller is further configured to:
determine a spread of the radiation field using one or more signals from the radiation detector; and
control the beam shaping apparatus to reduce the spread of the field when the determined spread of the radiation field is within a threshold distance from an edge of the radiation detector.

4. The radiotherapy apparatus of claim 1, wherein the controller is configured to:

control the beam shaping apparatus such that all of the radiation in the field of radiation is incident on the beam receiving apparatus.

5. The radiotherapy apparatus of claim 1, wherein, in the at least one non-coplanar, tilted, configuration, the controller is configured to follow an operational rule defining a limit of retraction of at least one beam shaping member of the beam shaping apparatus.

6. The radiotherapy apparatus of claim 5, wherein application of the operational rule is dependent on whether the radiation source is in the coplanar configuration or the at least one non-coplanar, tilted, configuration.

7. The radiotherapy apparatus of claim 5, wherein the at least one beam shaping member is at least one of a diaphragm or a leaf of a multi-leaf collimator (MLC).

8. The radiotherapy apparatus of claim 5, wherein the beam shaping apparatus is a multi-leaf collimator (MLC) and the limit is applied such that, in the at least one non-coplanar, tilted, configuration, one leaf, or a plurality of adjacent leaves, of the MLC have a limit of retraction such that the one leaf or the plurality of adjacent leaves does not retract from a maximum extension into the radiation field.

9. The radiotherapy apparatus of claim 1, wherein the controller is further configured to:
control the radiation source.

10. The radiotherapy apparatus of claim 1, wherein the controller is configured to:
control the beam shaping apparatus to adjust an angle of the field of radiation relative to a rotation axis.

11. The radiotherapy apparatus of claim 1, wherein the radiation source and beam receiving apparatus are mounted on opposite sides of the rotatable gantry.

12. The radiotherapy apparatus of claim 1, wherein, in the at least one non-coplanar, tilted, configuration, the radiation source is configured to direct the field of radiation at an oblique angle relative to the rotation axis.

13. The radiotherapy apparatus of claim 12, wherein the controller is configured to:
control the beam shaping apparatus to modify the oblique angle of the field of radiation relative to the rotation axis when the radiation source is in the at least one non-coplanar, tilted, configuration.

14. A method of controlling a field of radiation produced by a radiation source of a radiotherapy apparatus comprising a rotatable gantry configured to rotate about a rotation axis and a beam receiving apparatus, the method comprising:
switching the radiation source between a coplanar configuration and a non-coplanar configuration, wherein, in the coplanar configuration, the radiation source is positioned to rotate about the rotation axis and to rotate in a first plane, and wherein, in the non-coplanar configuration, the radiation source is non-coplanar with respect to the first plane such that the field of radiation produced by the radiation source is directed at an oblique angle relative to the first plane and the rotation axis, and wherein, in the non-coplanar configuration, the radiation source is positioned to rotate in a respective second plane parallel to and displaced from the first plane, and wherein the beam receiving apparatus remains in the same place relative to the rotatable gantry when the radiation source is in the coplanar configuration or the non-coplanar configuration;
applying a limit to the field of radiation produced by the radiation source based on whether the radiation source is configured in the coplanar configuration or the non-coplanar configuration, wherein the limit is applied to the field of radiation such that the radiation produced by the radiation source is directed towards the beam receiving apparatus in each of the coplanar configuration and at least one non-coplanar, tilted, configuration;
applying the limit when the radiation source is in the non-coplanar configuration to prevent the field of radiation from extending beyond the beam receiving apparatus; and
removing the limit when the radiation source is in the coplanar configuration.

15. The method of claim 14, wherein the field of radiation is limited such that all of the radiation in the field of radiation is incident on the beam receiving apparatus.

16. The method of claim 14, wherein the field of radiation is controlled by applying an operational rule defining a limit of retraction of at least one beam shaping member of a beam shaping apparatus.

17. The method of claim 16, wherein application of the operational rule is dependent on whether the radiation source is in the coplanar configuration or the non-coplanar configuration.

18. The method of claim 16, wherein the beam shaping apparatus is a multi-leaf collimator (MLC), and wherein the limit is applied such that, in the non-coplanar configuration, one leaf, or a plurality of adjacent leaves, of the MLC have a limit of retraction such that the one leaf or the plurality of adjacent leaves do not retract from a maximum extension into the radiation field.

19. A non-transitory computer-readable medium comprising instructions that, when executed by one or more processors of a radiotherapy apparatus comprising a rotatable gantry configured to rotate about a rotation axis and a beam receiving apparatus, cause the one or more processors to:
switch a radiation source between a coplanar configuration and a non-coplanar configuration, wherein, in the coplanar configuration, the radiation source is positioned to rotate about the rotation axis and to rotate in a first plane, and wherein, in the non-coplanar configuration, the radiation source is non-coplanar with respect to the first plane such that a field of radiation produced by the radiation source is directed at an oblique angle relative to the first plane and the rotation axis, and wherein, in the non-coplanar configuration, the radiation source is positioned to rotate in a respective second plane parallel to and displaced from the first plane, and wherein the beam receiving apparatus remains in the same place relative to the rotatable gantry when the radiation source is in the coplanar configuration or the non-coplanar configuration;
apply a limit to the field of radiation produced by the radiation source based on whether the radiation source is configured in the coplanar configuration or the non-coplanar configuration, wherein the limit is applied to the field of radiation such that the radiation produced by the radiation source is directed towards the beam receiving apparatus in each of the coplanar configuration and at least one non-coplanar, tilted, configuration;
apply the limit when the radiation source is in the non-coplanar configuration to prevent the field of radiation from extending beyond the beam receiving apparatus; and
remove the limit when the radiation source is in the coplanar configuration.

* * * * *